(12) United States Patent
Gindele et al.

(10) Patent No.: US 6,476,865 B1
(45) Date of Patent: Nov. 5, 2002

(54) SPARSELY SAMPLED IMAGE SENSING DEVICE WITH COLOR AND LUMINANCE PHOTOSITES

(75) Inventors: Edward B. Gindele, Rochestre, NY (US); Andrew C. Gallagher, Brockport, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/800,875

(22) Filed: Mar. 7, 2001

(51) Int. Cl.[7] .......................... H04N 3/14; H04N 5/335; H04N 9/04; H04N 9/083
(52) U.S. Cl. ........................................ 348/277; 348/273
(58) Field of Search ................................. 348/270, 271, 348/272, 273, 222, 234, 277, 279; 257/440

(56) References Cited

U.S. PATENT DOCUMENTS

| 3,971,065 A | | 7/1976 | Bayer | |
| 4,630,307 A | * | 12/1986 | Cok | 345/643 |
| 5,323,233 A | | 6/1994 | Yamagami et al. | |
| 5,382,976 A | * | 1/1995 | Hibbard | 348/266 |
| 5,652,621 A | | 7/1997 | Adams, Jr. et al. | |
| 5,808,674 A | * | 9/1998 | Adams et al. | 348/273 |
| 5,880,782 A | * | 3/1999 | Koyanagi et al. | 348/169 |
| 5,990,950 A | * | 11/1999 | Addison | 348/273 |

* cited by examiner

*Primary Examiner*—Wendy R. Garber
*Assistant Examiner*—Matthew L Rosendale
(74) *Attorney, Agent, or Firm*—Thomas H. Close

(57) ABSTRACT

An image sensing device having an array of light-sensitive elements, including: a first type of element sensitive to a spectral region corresponding to luminance; a second type of element sensitive primarily to red light; a third type of element sensitive primarily to green light; and a fourth type of element sensitive primarily to blue light, the four types of elements occurring in repeating patterns.

10 Claims, 10 Drawing Sheets

FIG. 2b (Motion Art)

|   |   |   |   |   |   |   |   |
|---|---|---|---|---|---|---|---|
| R | G | R | G | R | G | R | G |
| X | B | X | B | X | B | X | B |
| R | G | R | G | R | G | R | G |
| X | B | X | B | X | B | X | B |
| R | G | R | G | R | G | R | G |
| X | B | X | B | X | B | X | B |
| R | G | R | G | R | G | R | G |
| X | B | X | B | X | B | X | B |

|  |  |  |  |  |
|---|---|---|---|---|
| $L_1$ | R | $L_3$ | R | $L_5$ |
| B | $G_7$ | $B_8$ | $G_9$ | B |
| $L_{11}$ | $R_{12}$ | $L_{13}$ | $R_{14}$ | $L_{15}$ |
| B | $G_{17}$ | $B_{18}$ | $G_{19}$ | B |
| $L_{21}$ | R | $L_{23}$ | R | $L_{25}$ |

FIG. 7

| $R_1$ | L | $R_3$ | L | $R_5$ |
| G | $B_7$ | $G_8$ | $B_9$ | G |
| $R_{11}$ | $L_{12}$ | $R_{13}$ | $L_{14}$ | $R_{15}$ |
| G | $B_{17}$ | $G_{18}$ | $B_{19}$ | G |
| $R_{21}$ | L | $R_{23}$ | L | $R_{25}$ |

FIG. 8

| $B_1$ | G | $B_3$ | G | $B_5$ |
| --- | --- | --- | --- | --- |
| L | $R_7$ | $L_8$ | $R_9$ | L |
| $B_{11}$ | $G_{12}$ | $B_{13}$ | $G_{14}$ | $B_{15}$ |
| L | $R_{17}$ | $L_{18}$ | $R_{19}$ | L |
| $B_{21}$ | G | $B_{23}$ | G | $B_{25}$ |

FIG. 9

|       |       |          |          |          |
|-------|-------|----------|----------|----------|
| $G_1$ | B     | $G_3$    | B        | $G_5$    |
| R     | $L_7$ | $R_8$    | $L_9$    | R        |
| $G_{11}$ | $B_{12}$ | $G_{13}$ | $B_{14}$ | $G_{15}$ |
| R     | $L_{17}$ | $R_{18}$ | $L_{19}$ | R     |
| $G_{21}$ | B     | $G_{23}$ | B        | $G_{25}$ |

|       |       |       |
|-------|-------|-------|
| $G_1$ | $B_2$ | $G_3$ |
| $R_4$ | $X_5$ | $R_6$ |
| $G_7$ | $B_8$ | $G_9$ |

FIG. 10

SPARSELY SAMPLED IMAGE SENSING DEVICE WITH COLOR AND LUMINANCE PHOTOSITES

FIELD OF THE INVENTION

The invention relates generally to the field of image capture, and more specifically to an image sensing device with different color types of photosites.

BACKGROUND OF THE INVENTION

Electronic image sensing devices have employed a technique of sparsely sampling photographic images with an arrangement of photosites having different color responses to light. The term sparsely sampling as used herein refers to the fact that all colors are not sensed at all photosites in the image sensing device. In 1975 Bayer disclosed a sparsely sampled image sensing device in the form of a color filter array of photosites in U.S. Pat. No. 3,971,065 issued Jul. 20, 1976 to Bayer. The image sensing device described by Bayer was configured in a rectangular array of photosites with luminance sensitive photosites occurring every other photosite of every row of photosite with the pattern of luminance sensitive photosites staggered by one pixel in adjacent rows of photosite. Thus the luminance sensitive photosites formed a checkerboard pattern. The other photosites of Bayer's image sensing device used two types of chrominance, or color, sensitive photosites with a first chrominance photosite type used in the odd rows of photosites, and a second chrominance photosite type used in the even rows of photosites.

Bayer also disclosed an alternative configuration for a sparsely sampling image sensing device in U.S. Pat. No. 3,971,065 that over time has proven to be more useful. In this alternative configuration, green sensitive photosites are used to sense the luminance signal and red and blue sensitive photosites are used for the two chrominance types of photosites as shown in FIG. 2a. The advantage of Bayer's alternative configuration is a sensor with nearly equalized photo response between the three types of photo elements, i.e. the three types of photosites saturate at nearly the same incident light level when exposed to white light. A disadvantage of both the Bayer configurations is evident when over exposure conditions arise. Since the green sensitive photosites have a closer relationship to the image luminance signal, many real world objects have more green image content than red or blue image content. Consequently, if a given scene is overexposed, the green sensitive photosites generally saturate (reach the maximum possible signal strength) faster than the red or blue sensitive photosites. The resulting pixel values corresponding to the saturated photosites are clipped (reach a maximum pixel value) resulting in a loss of spatial detail. FIG. 2b shows the Bayer pattern with X's at the locations of the saturated green photosites. These saturated green photosites may obscure image detail. Not only is there a loss of spatial detail but there is also a loss of green color information at these photosites.

U.S. Pat. No. 5,323,233 issued Jun. 21, 1994 to Yamagami et al. discloses an image sensing device color filter array of photosites with a different configuration as a variation on Bayer's pattern. The Yamagami pattern of photosites is shown in FIG. 3a with the Y labeled photosites responding to luminance light, and R, G, and B labeled photosites responding to red, green, and blue light respectively. The Yamagami pattern contains 50% luminance photosites, 25% green photosites, 12½% red photosites, and 12½% blue photosites. The Yamagami pattern for overexposed conditions is shown in FIG. 3b with saturated luminance photosites indicated by X's. The red, green, and blue photosites may still produce modulated signals. However, for overexposed conditions the Yamagami pattern does suffer a loss of spatial resolution due to the fact that 50% of the array are luminance response photosites.

There is a need therefore for an improved pattern of photosites for a image sensing device that employs a sparsely sampling technique.

SUMMARY OF THE INVENTION

The need is met according to the present invention by providing an image sensing device having an array of light-sensitive elements, including a first type of element sensitive to a spectral region corresponding to luminance; a second type of element sensitive primarily to red light; a third type of element sensitive primarily to green light; and a fourth type of element sensitive primarily to blue light, the four types of elements occurring in repeating patterns. In a preferred embodiment, the four types of elements of the image sensing device which occur in repeating patterns can be configured such that over at least a major portion of the array all four types of elements occur at every other element position along both of two orthogonal directions of the array of light-sensitive elements.

ADVANTAGES

An advantage of the present invention that the image sensing device minimizes the loss of spatial detail for overexposed conditions.

BRIEF DESCRIPTION OF THE DRAWINGS

FIG. 1 is a diagram showing the photosite pattern according to the invention;

Figures 2A, 2B:
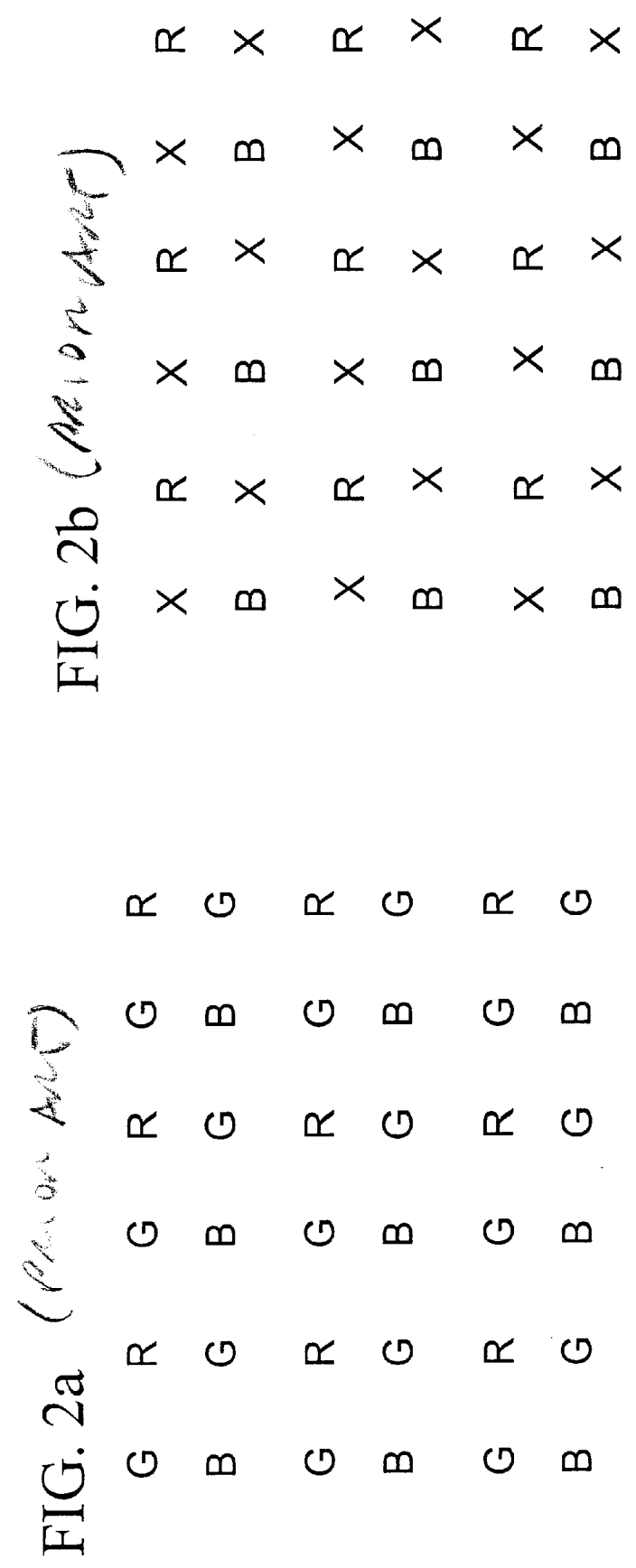

FIG. 2a is a diagram showing the prior art Bayer photosite pattern;

FIG. 2b is a diagram showing the prior art Bayer photosite pattern for overexposure conditions;

FIG. 3a is a diagram showing the prior art Yamagami photosite pattern;

FIG. 3b is a diagram showing the prior art Yamagami photosite pattern for overexposure conditions;

FIG. 4 is a diagram showing the photosite pattern according to the invention for overexposed conditions;

FIG. 6 is a diagram of pixels used by the CFA interpolator 26 to interpolate pixel values corresponding to the luminance photosites;

FIG. 7 is a diagram of pixels used by the CFA interpolator 26 to interpolate pixel values corresponding to the red photosites;

FIG. 8 is a diagram of pixels used by the CFA interpolator 26 to interpolate pixel values corresponding to the blue photosites;

FIG. 9 is a diagram of pixels used by the CFA interpolator 26 to interpolate pixel values corresponding to the green photosites; and FIG. 10 is a diagram of pixels used by the CFA interpolator 26 to interpolate pixel values corresponding to the luminance photosites when the luminance pixels are clipped.

DETAILED DESCRIPTION OF THE INVENTION

Figure 5:
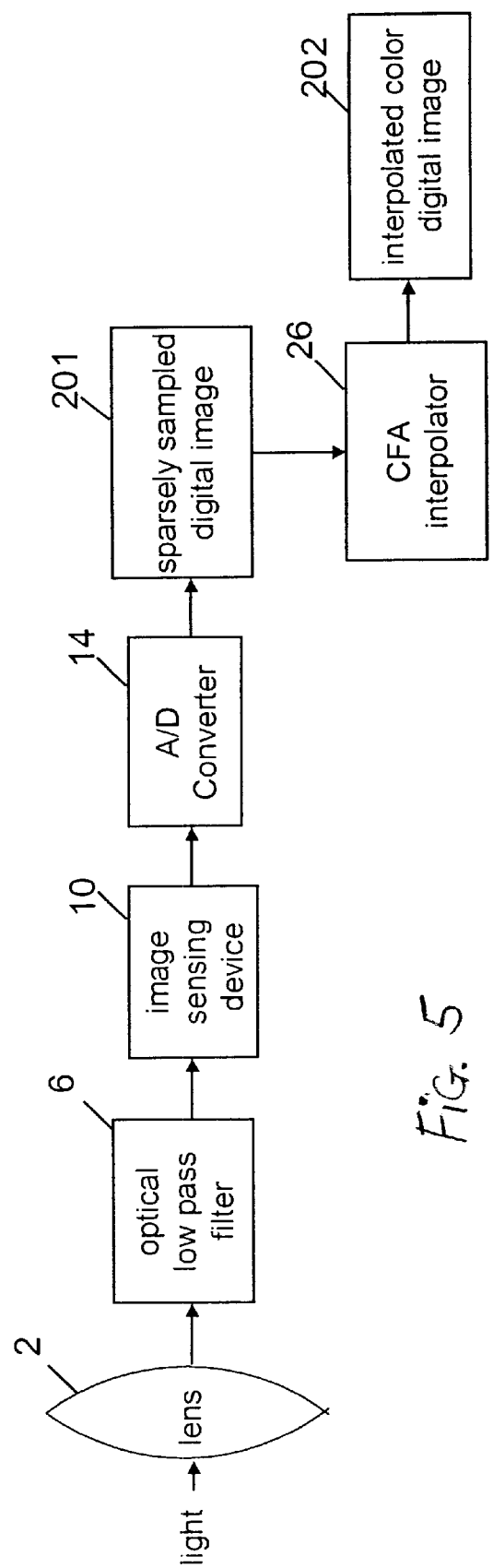
FIG. 5 is a block diagram of a digital imaging system utilizing an image sensing device with the photosite pattern and a CFA interpolator 26 according to the invention.

Image sensing devices, such as a charge-coupled device (CCD) and CMOS image sensors, are commonly found in such products as digital cameras, scanners, and video cameras. Many image sensing devices employ an array of color filters (color filter array (CFA)), to alter the color response to light of different light sensitive elements or photosites. Thus for the geometrical locations of the photosites in a sensed image, only one characteristic response to light or color is sampled. Hence, the image sensing devices which employ a color filter array are termed sparsely sampled image sensing devices. Digital pixel values (pixels) are derived from the electronic signals produced by the photosites with electronic analog-to-digital converting circuitry. Pixels derived from the signal produced by a photosite type that has a primarily red color response to light are termed red pixels. Similarly, green and blue pixels have corresponding photosite types responsive primarily to green and blue light respectively. Luminance pixels have corresponding photosite types responsive to red, green, and blue (white) light.

Figure 1:
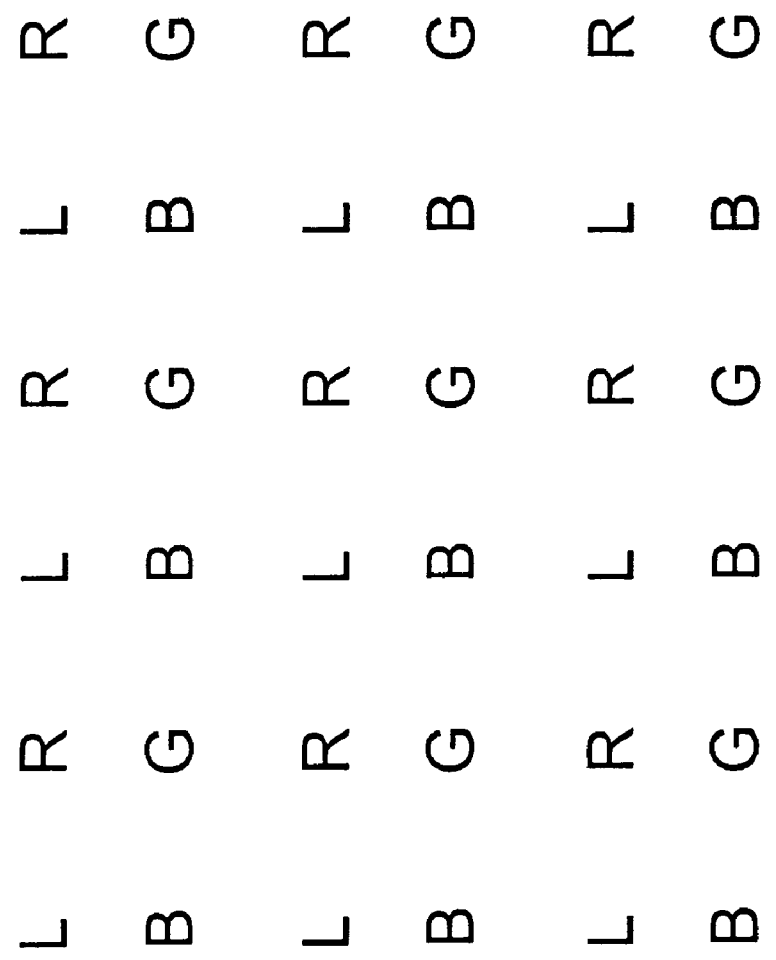

The present invention employs a color filter array CFA pattern of light sensitive elements as shown in FIG. 1. The photosite locations labeled with an L are sensitive to white light and generate luminance pixel data. Similarly, the photosite locations labeled with R, G, and B are sensitive primarily to red, green, and blue light and correspondingly generate red, green, and blue pixel data. Each of the four types of photosites are arranged in a rectangular pattern of every other photosite of every other row of photosites such that over at least a major portion of the array, all four types of elements occur at every other element position along both of two orthogonal directions of the array of light-sensitive elements. Note that each of the four photosite types are represented with equal frequency, i.e. each photosite type constitutes 25% of the total of photosites.

An important aspect of the present invention is evident for overexposure conditions. If too much light is received by the image sensing device, the luminance photosites will saturate, i.e. the luminance photosites reach the maximum signal condition before the red, green, and blue photosites. When an overexposure condition occurs, the corresponding luminance pixel values become clipped, i.e. they assume the maximum numerical value possible. In a typical sensed image, some of the luminance photosites will saturate while other receiving less light will not. Thus the saturation condition is experienced locally. FIG. 4 shows the CFA pattern of photosites for a local region of the image sensing device that has driven the luminance photosites into saturation by overexposure. The overexposed photosites are labeled with X's. Note that the red, green, and blue photosites may still record signal variations as they may not have been saturated by overexposure. Thus the present invention minimizes the loss of spatial detail for overexposed conditions by virtue of the fact that only 25% of the photosites are luminance photosites.

Imaging devices employing electronic sensors are well known, therefore the present description will be directed in particular to elements forming part of, or cooperating more directly with, apparatus in accordance with the present invention. Elements not specifically shown or described herein may be selected from those known in the art. Note that as used herein, the term image is a two dimensional array of pixel values. An image may be a two dimensional subset of another image. The present invention can be implemented in whole or in part within a digital camera.

The essential elements of the present invention are shown as a functional block diagram in FIG. 5. Light from an object or scene is incident upon a lens 2, forming a photographic image on the image sensing device 10 such as a charged-coupled device (CCD). Note that other devices, such as CMOS devices, may be used as the image sensing device 10. An optical low pass filter 6, placed between the lens 2 and the image sensing device 10 performs a slight blurring of the imaged light in order to reduce the occurrence of aliasing. An A/D converter 14 receives the voltage signal corresponding to the imaged light from the image sensing device 10 and produces an image signal corresponding to the voltage signal. The output of the A/D converter 14 is a sparsely sampled digital image 201. A sparsely sampled digital image is defined as a digital image that was captured with an image sensing device having a single image sensor with multiple types of photosites. The CFA interpolator 26 receives the sparsely sampled digital image 201 from the A/D converter 14 and generates an interpolated color digital image 202 by applying a color filter array CFA interpolation filter to the sparsely sampled digital image 201. The CFA interpolator 26 generates color pixel values for pixel locations for which the corresponding color was not sensed by the image sensing device 10. For example, the CFA interpolator 26 generates red pixel values for pixel locations corresponding to green photosites. Thus the interpolated color digital image 202 has defined red, green, and blue pixel values for all pixel locations.

The A/D converter 14 shown in FIG. 5 converts the voltage signal produced by the image sensing device 10 into an image signal, i.e. a stream of digital pixel values corresponding to the voltage signal produced by the photosites of the image sensing device 10. More specifically, the A/D converter 14 converts the voltage signal, nearly linear with respect to the intensity of the incident light, from the image sensing device 10 to a discrete digital image signal, e.g. a 10 bit signal where the linear encoded values range from 0 to 1023. The A/D converter 14 may also perform processing to convert the linear code value domain image signal to a nonlinear code value domain image signal, such as an 8 bit logarithmic signal as is commonly performed in the art.

Generally, the CFA interpolator 26 operates by considering the pixel values of the corresponding photosite and the pixel values of associated surrounding photosites. While a variety of known CFA interpolation filters may be used, the present invention uses a modified version of the CFA interpolation filter disclosed by Adams et al. in U.S. Pat. No. 5,652,621 issued Jul. 29, 1997 to Adams, Jr. et al. The CFA interpolator 26 produces the interpolated color digital image 202 from the sparsely sampled digital image 201 in a three step procedure. In the first interpolation step, a first interpolated pixel value for all four types of pixels is generated. Although a color digital image can be constructed directly from these first interpolated pixel values, the present invention uses the first interpolated pixel values in a second interpolation step to generate color difference pixel values. In a third interpolation step, the color difference pixel values and the first interpolated luminance pixel values are used to generate second, or final, interpolation pixel values for improved results.

In the first interpolation step, a first interpolation pixel value or missing color pixel value, i.e. a color pixel value not generated directly by a photosite sensing the corresponding color of light, is generated by considering neighboring pixel values. This interpolation step is performed for each missing pixel value at each pixel location. Therefore, first interpolated red R', green G', and blue B' pixel values are generated at pixel locations corresponding to the luminance photosites. Similarly, first interpolated luminance L', green G', and blue B' pixel values are generated at pixel locations corresponding to the red photosites. First interpolated luminance L', red R', and blue B' pixel values are generated at pixel locations corresponding to the green photosites. First interpolated luminance L', red R', and green G' pixel values are generated at pixel locations corresponding to the blue photosites.

FIG. 6 shows the pattern of pixels for generating first interpolating pixel values for red R', green G' and blue B' pixels at a pixel location corresponding to a luminance photosite. The first interpolated red pixel value $R'_{13}$ corresponding to the pixel location at $L_{13}$ is calculated in two terms. The first term is an average of two nearest neighboring red pixel values $R_{12}$ and $R_{14}$. The second term is a Laplacian pixel value given by subtracting the average of the two nearest neighboring luminance pixel values $L_{11}$ and $L_{15}$ from the center luminance pixel value $L_{13}$ that are in a line, in this case a horizontal line, as the nearest neighboring red pixels. The first interpolated blue pixel value $B'_{13}$ corresponding to the pixel location $L_{13}$ is calculated in similar fashion with the luminance and blue pixel values sampled in the vertical direction about the center luminance pixel $L_{13}$.

The green photosites do not line up in either a horizontal or vertical line about the luminance photosites. However, the green photosites do lineup with the luminance photosites along the two diagonal directions. One of the diagonal sets of pixels is used to calculate the first interpolated green pixel value based on the magnitude of the gradients along the two diagonal directions. Specifically, the absolute value of the difference between pixels $G_7$ an $G_{19}$ (gradient pixel value) is compared with the absolute value of the difference between pixels $G_{19}$ an $G_{17}$ (gradient pixel value) shown in FIG. 6. If the magnitude of the gradient pixel value formed from pixels $G_7$ and $G_{19}$ is less than the magnitude of the gradient pixel value formed from pixels $G_9$ and $G_{17}$, then pixels $L_1$, $L_{13}$, $L_{25}$, $G_7$, and $G_{19}$ are used in to calculate the green first interpolated pixel value $G_{13}$ corresponding to the pixel location $L_{13}$. Otherwise, pixels $L_5$, $L_{13}$, $L_{21}$, $G_9$, and $G_{17}$ are used in to calculate the first interpolated green pixel value $G'_{13}$ corresponding to the pixel location $L_{13}$. Equation (1) describes the mathematical formula for the first interpolated red, green, and blue pixel values $R'_{13}$, $G'_{13}$, and $B'_{13}$ respectively corresponding to the pixel location $L_{13}$.

$$R'_{13}=(R_{12}+R_{14})/2+(-L_{11}-2L_{13}-L_{15})/4$$

$$B'_{13}=(B_8+B_{18})/2+(-L_3-2L_{13}-L_{23})/4$$

$$G'_{13}=(G_7+G_{19})/2+(-L_1-2L_{13}-L_{25})/4 \text{ for } |G_7-G_{19}|<|G_9-G_{17}|$$

$$G'_{13}=(G_9+G_{17})/2+(-L_5-2L_{13}-L_{21})/4 \text{ for } |G_9-G_{17}|<=|G_7-G_{19}| \quad (1)$$

FIG. 7 shows the pattern of pixels used for interpolating the first interpolated luminance $L'_{13}$, green $G'_{13}$, and blue $B'_{13}$ pixel values corresponding to the pixel location $R_{13}$. For this case, the red and green pixels line up along the vertical direction while the red and luminance pixels line up along the horizontal direction. The blue and red pixels line up along the two diagonal directions. Equation (2) describes the mathematical formula for the first interpolated luminance, green, and blue pixel values $L'_{13}$, $G'_{13}$, and $B'_{13}$ respectively, corresponding to the pixel location $R_{13}$.

$$L'_{13}=(L_{12}+L_{14})/230 \, (-R_{11}2R_{13}-R_{15})/4$$

$$G'_{13}=(G_8+G_{18})/230 \, (-R_3-2R_{13}-R_{23})/4$$

$$B'_{13}=(B_7+B_{19})/230 \, (-R_1-2R_{13}-R_{25})/4 \text{ for } |B_7-B_{19}|<|B_9-B_{17}|$$

$$B'_{13}=(B_9+B_{17})/230 \, (-R_5-2R_{13}-R_{21})/4 \text{ for } |B_9-B_{17}|<=|B_7-B_{19}| \quad (2)$$

FIG. 8 shows the pattern of pixels used for interpolating the first interpolated luminance $L'_{13}$, green $G'_{13}$, and red $R'_{13}$ pixel values corresponding to the pixel location $B_{13}$. For this case, the luminance and blue pixels line up along the vertical direction while the green and blue pixels line up along the horizontal direction. The blue and red pixels line up along the two diagonal directions. Equation (3) describes the mathematical formula for the first interpolated red, green, and luminance pixel values $R'_{13}$, $G'_{13}$, and $L'_{13}$ respectively corresponding to the pixel location $B_{13}$.

$$G'_{13}=(G_{12}+G_{14})/2+(-B_{11}-2B_{13}-B_{15})/4$$

$$L'_{13}=(L_8+L_{18})/2+(-B_3-2B_{13}-B_{23})/4$$

$$R'_{13}=(R_7+R_{19})/2+(-B_1-2B_{13}-B_{25})/4 \text{ for } |R_7-R_{19}|<|R_9-R_{17}|$$

$$R'_{13}(R_9+R_{17})/2+(-B_5-2B_{13}-B_{21})/4 \text{ for } |R_9-R_{17}|<=|R_7-R_{19}| \quad (3)$$

FIG. 9 shows the pattern of pixels used for interpolating the first interpolated luminance $L'_{13}$, red $R'_{13}$, and blue $B'_{13}$ pixel values corresponding to the pixel location $G_{13}$. For this case, the red and green pixels line up along the vertical direction while the green and blue pixels line up along the horizontal direction. The green and luminance pixels line up along the two diagonal directions. Equation (4) describes the mathematical formula for the first interpolated red, blue, and luminance pixel values $R'_{13}$, $B'_{13}$, and $L'_{13}$ respectively corresponding to the pixel location $G_{13}$.

$$B'_{13}=(B_{12}+B_{14})/2+(-G_{11}-2G_{13}-G_{15})/4$$

$$R'_{13}=(R_8+R_{18})/2+(-G_3-2G_{13}-G_{23})/4$$

$$L'_{13}=(L_7+L_{19})/2+(-G-2G_{13}-G_{25})/4 \text{ for } |L_7-L_9|<|L_9-L_{17}|$$

$$L'_{13}=(L_9+L_{17})/2+(-G_5-2G_{13}-G_{21})/4 \text{ for } |L_9-L_{17}|<=|L_7-L_{19}| \quad (4)$$

In the second interpolation step, two color difference pixel values are generated for each pixel location, i.e. a green-magenta pixel value (GM') and an illuminant pixel value (ILL'). The mathematical formulas for calculating these two color difference pixel values are given in Equation (5)

$$GM'=(2G'-R'-B')/4$$

$$ILL'=(B'-R')/2 \quad (5)$$

where the R', G', and B' variables represent the interpolated red, green, and blue pixel values respectively corresponding to a luminance photosite. For the red, green, and blue photosite locations, Equation (5) is used to calculate a GM' and ILL' pixel value, however, when possible, the original pixel values rather than the first interpolated pixel values are used. For example, at the red photosites, the original red pixel values R and the interpolated green G' and blue B' pixel values are used in Equation (5).

After the second step, an L', GM', and ILL' pixel is defined for all pixel locations. In the third interpolation step, the L', GM', and ILL' pixel values are used to generate the set of second interpolated red, green, and blue pixel values R", G", and B" respectively. The inverse transform of Equation (5) is used to generate the R", G"", and B"" pixel values given by Equation (6).

$$R''=L'-(2GM')/3-ILL'$$

$$B''=L'-(2GM')/3+ILL'$$

$$G''=L'+(4GM')/3 \quad (6)$$

At the luminance photosite locations, the original L pixel values re used in Equation (6) in place of the L' variable. The original pixel values R, and B are uses as the final interpolated pixel values at the locations of the red, green, and blue photosites respectively. For example, the second interpolated red pixel values R" form the red pixel values of the interpolated color digital image 202 for the luminance, green, and blue photosite pixel locations.

Figure 10:
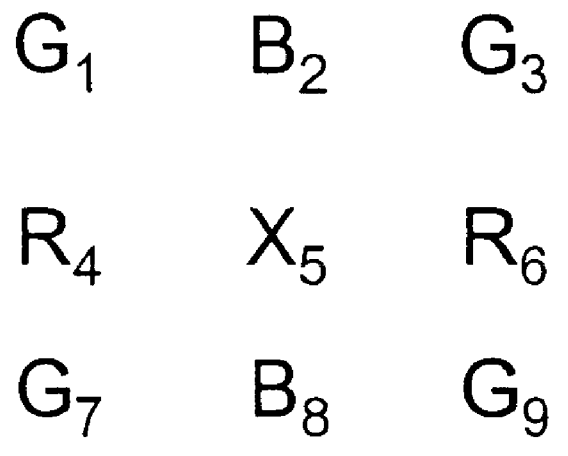

As shown in FIG. 4, when the imaging sensing device 10 experiences an overexposure condition resulting from too much light received, the luminance pixel values clip to the maximum allowable pixel value as produced by the A/D converter 26. The present invention remedies the overexposure condition by using a nearest neighbor interpolation method. For the clipped luminance pixel location indicated by the X's in FIG. 10, the second interpolated blue pixel value B" is calculated by averaging the two adjacent vertical original blue pixel values. Similarly, the second interpolated red pixel value R" is calculated by averaging the two adjacent horizontal original red pixel values. The second interpolated green pixel value G" is calculated by first comparing the magnitude of the different between the two sets of diagonal green pixel values. The two diagonal pairs of green pixel values with the lesser magnitude gradient pixel values are averaged to calculate the second interpolated green pixel value G". Equation (7) describes the mathematical calculation of second interpolated red R", green G", and blue B" pixel values for the clipped pixel corresponding to the pixel location $X_5$ shown in FIG. 10.

$$R_5''=(R_4+R_6)/2$$

$$B_5''=(B_2+B_8)/2$$

$$G_5''=(G_1+G_9)/2 \text{ for } |G_1-G_9|<|G_3-G_7|$$

$$G_5''=(G_3+G_7)/2 \text{ for } |G_3-G_7|<=|G_1-G_9| \quad (7)$$

For the color pixel locations surrounding the clipped luminance pixel the first interpolated pixel values are used. For example, at pixel location $G_1$, R' and B' are used as the final interpolated pixel values R" and B" respectively. Similarly, at pixel location $R_1$, G' and B' are used as the second interpolated pixel values G" and B" respectively. At pixel location $B_1$, G' and R' are used as the second interpolated pixel values G" and R" respectively.

The invention has been described in detail with particular reference to certain preferred embodiments thereof, but it will be understood that variations and modifications can be effected within the spirit and scope of the invention.

PARTS LIST 2 lens
6 optical lowpass filter
10 image sensing device
14 A/D converter
26 CFA interpolator
201 sparsely sampled digital image
202 interpolated color digital image

What is claimed is:

1. An image sensing device having an array of light-sensitive elements, comprising a first type of element sensitive to a spectral region corresponding to luminance; a second type of element sensitive primarily to red light; a third type of element sensitive primarily to green light; and a fourth type of element sensitive primarily to blue light, the four types of elements occurring in repeating patterns such that over at least a major portion of the array, all four types of elements occur in equal numbers.

2. The image sensing device claimed in claim 1, wherein the four types of elements occurring in repeating patterns are such that over at least a major portion of the array all four types of elements occur at every other element position along both of two orthogonal directions of the array of light-sensitive elements.

3. A method of capturing a color digital image, comprising the steps of:

a) providing an image sensing device having an array of light-sensitive elements, which array includes at least a first type of element sensitive to a spectral region corresponding to luminance; a second type of element sensitive primarily to red light; a third type of element sensitive primarily to green light; and a fourth type of element sensitive primarily to blue light, the four types of elements occurring in repeating patterns;

b) employing the image sensing device to produce a sparsely sampled digital image; and c) interpolating missing color pixel values in the sparsely sampled digital image to generate the color digital image having a red, green and blue pixel value for each location in the array by employing a first interpolation technique that uses neighboring luminance values when the neighboring luminance values are not clipped, and a second interpolation technique that does not use neighboring luminance values when the neighboring luminance values are clipped.

4. The method claimed in claim 3, wherein the four types of elements occurring in repeating patterns are such that over at least a major portion of the array all four types of elements occur at every other element position along both of two orthogonal directions of the array of light-sensitive elements.

5. The method claimed in claim 3, wherein the image sensing device is in a camera.

6. The method claimed in claim 5, wherein the interpolation step is performed in the camera.

7. The method claimed in claim 3, wherein the interpolation step includes the steps of:

c1) calculating a first set of interpolated pixel values for each color at each pixel location;

c2) calculating color difference pixel values for each pixel location using the first set of interpolated pixel values; and c3) calculate a final set of interpolated pixel values using the color difference pixel values.

8. The method claimed in claim 7, wherein the first set of interpolated pixel values are calculated by computing a Laplacian pixel value for pixels of one color and adding the Laplacian pixel value to a pixel value of a different color.

9. The method claimed in claim 7, wherein the final set of interpolated pixel values are calculated for clipped pixels using a nearest neighbor averaging technique.

10. The method claimed in claim 7, wherein the luminance pixel values and the color difference pixel values are used to calculate the final set of interpolated pixel values.

* * * * *